United States Patent
Seatter

(10) Patent No.: US 6,820,507 B2
(45) Date of Patent: Nov. 23, 2004

(54) APPARATUS FOR EXTRACTING A REPRESENTATIVE SAMPLE OF WATER, OIL AND SEDIMENT FROM A CONTAINER

(76) Inventor: Norman Eugene Seatter, Box 996, Slave Lake, Alberto (CA), T0G 2A0

( * ) Notice: Subject to any disclaimer, the term of this patent is extended or adjusted under 35 U.S.C. 154(b) by 0 days.

(21) Appl. No.: 10/320,838

(22) Filed: Dec. 16, 2002

(65) Prior Publication Data

US 2003/0115973 A1 Jun. 26, 2003

(30) Foreign Application Priority Data

Dec. 24, 2001 (CA) .............................................. 2366518

(51) Int. Cl.⁷ .............................................. G01N 1/16
(52) U.S. Cl. .............................. 73/863.81; 73/863.81; 73/863.83; 73/864.51; 73/864.64; 73/864.72; 73/864.73; 73/863.33; 73/863.34; 73/863.35; 73/863.84; 222/633
(58) Field of Search .......................... 73/861.81, 861.83, 73/864.51, 864.64, 864.72, 864.73, 863.33, 864.34, 864.35, 863.84; 222/633

(56) References Cited

U.S. PATENT DOCUMENTS

| | | | | |
|---|---|---|---|---|
| 2,896,825 A | * | 7/1959 | Jackson | 222/211 |
| 2,981,444 A | * | 4/1961 | Root | 222/632 |
| 4,299,795 A | | 11/1981 | Bates | |
| 4,340,464 A | | 7/1982 | Aiba et al. | |
| 4,348,909 A | | 9/1982 | Kluth et al. | |
| 4,526,305 A | * | 7/1985 | Lykes | 222/632 |
| 4,925,128 A | * | 5/1990 | Brody | 222/211 |
| 4,941,360 A | * | 7/1990 | McClellan et al. | 73/864.34 |
| 5,237,878 A | * | 8/1993 | Hackenberg | 73/861.34 |
| 5,503,036 A | | 4/1996 | Nguyen et al. | |
| 5,603,342 A | | 2/1997 | Shambaugh | |
| 5,803,310 A | * | 9/1998 | Soon | 222/1 |
| 5,938,939 A | * | 8/1999 | Vial et al. | 210/767 |
| 5,960,530 A | | 10/1999 | Kerr et al. | |
| 5,971,234 A | * | 10/1999 | Mathison et al. | 222/633 |
| 5,996,424 A | * | 12/1999 | Tan et al. | 73/864.34 |
| 6,062,092 A | | 5/2000 | Weaver | |
| 6,076,410 A | * | 6/2000 | Renslow | 73/864.34 |

* cited by examiner

Primary Examiner—Hezron Williams
Assistant Examiner—André K. Jackson
(74) Attorney, Agent, or Firm—Christensen O'Connor Johnson Kindness PLLC

(57) ABSTRACT

A method and apparatus for extracting a representative sample of water, oil and sediment from a container. The apparatus is a container closure having a tube extending therethrough, such that fluids can be extracted from any closed container through the tube when closed by the closure. The tube has a first end and a second end. The first end is open to the flow of fluids and the second end is closed. Several radial inlet ports are position at spaced intervals along the tube between the closure and the second end of the tube. Fluids from the container enter the tube at several levels through different ones of the inlet ports, thereby providing a more representative sample.

2 Claims, 7 Drawing Sheets

APPARATUS FOR EXTRACTING A REPRESENTATIVE SAMPLE OF WATER, OIL AND SEDIMENT FROM A CONTAINER

FIELD OF THE INVENTION

The present invention relates to a method and an apparatus for extracting a representative sample of water, oil and sediment from a container and, in particular, a container containing fluids produced by an oil well.

BACKGROUND OF THE INVENTION

Most producing oil wells produce water and sediment along with oil. The percentage of water and sediment tends to increase over time as the oil well "matures". Whether an oil well remains economically viable at a given crude oil price, depends upon the relative percentages of water, oil and sediment produced; for it costs just as much to pump water and sediment from the oil well as it does to pump oil.

Most oil wells have installed sampling systems that systematically sample fluids produced by the oil well and store them in a collection container. The sample fluids are then poured from the collection container into a sample tube which is analyzed.

It has been determined that separation of the water, oil and sediment, is preventing a representative sample from being transferred from the collection container to the sample tube. This is causing gross inaccuracies in the water, oil and sediment data.

SUMMARY OF THE INVENTION

What is required is a method and an apparatus for extracting a representative sample of water, oil and sediment from a container.

According to one aspect of the present invention there is provided an apparatus for extracting a representative sample of water, oil and sediment from a container. The apparatus includes a container closure having a tube extending therethrough, such that fluids can be extracted from any closed container through the tube when closed by the closure. The tube has a first end and a second end. The first end is open to the flow of fluids and the second end is closed. Several radial inlet ports are positioned at spaced intervals along the tube between the closure and the second end of the tube. Fluids from the container enter the tube at several levels through different ones of the inlet ports, thereby providing a more representative sample.

According to another aspect of the present invention there is provided a method for extracting a representative sample of water, oil and sediment from a container. A first step involves providing a container having a container closure substantially as described above. A second step involves agitating the container to mix the fluids. A third step involves creating pressure within the container sufficient to cause the mixed fluids from the container to flow out of the first end of the tube. The fluids enter through the inlet ports at spaced intervals along the tube, thereby giving a more representative sample.

There are various ways that pressure can be created inside a container sufficient to cause fluids to flow out through the tube. Beneficial results have been obtained when the container is resiliently deformable. This enables pressure to be created by squeezing the container to force fluids to exit the container via the tube.

Although beneficial results may be obtained through the use of the method and apparatus, as described above, in order to obtain the most accurate results all inlet ports must contribute substantially equal amounts of fluids to the sample. It has been determined that the contribution of each of the inlet ports becomes more equal when the inlet ports have a combined flow capacity which is less than a flow capacity of the tube.

It has been determined that the above described method and apparatus is not only more accurate, it also eliminates the mess which was formerly associated with pouring fluids from collection containers into smaller sample tubes. The fluids coming out of the tube on the above described apparatus is a steady small stream which is much easier to control. The container can now be inverted after agitating and a representative sample squeezed into the sample tube.

BRIEF DESCRIPTION OF THE DRAWINGS

These and other features of the invention will become more apparent from the following description in which reference is made to the appended drawings, the drawings are for the purpose of illustration only and are not intended to in any way limit the scope of the invention to the particular embodiment or embodiments shown, wherein.

DETAILED DESCRIPTION OF THE PREFERRED EMBODIMENT

Figure 1:
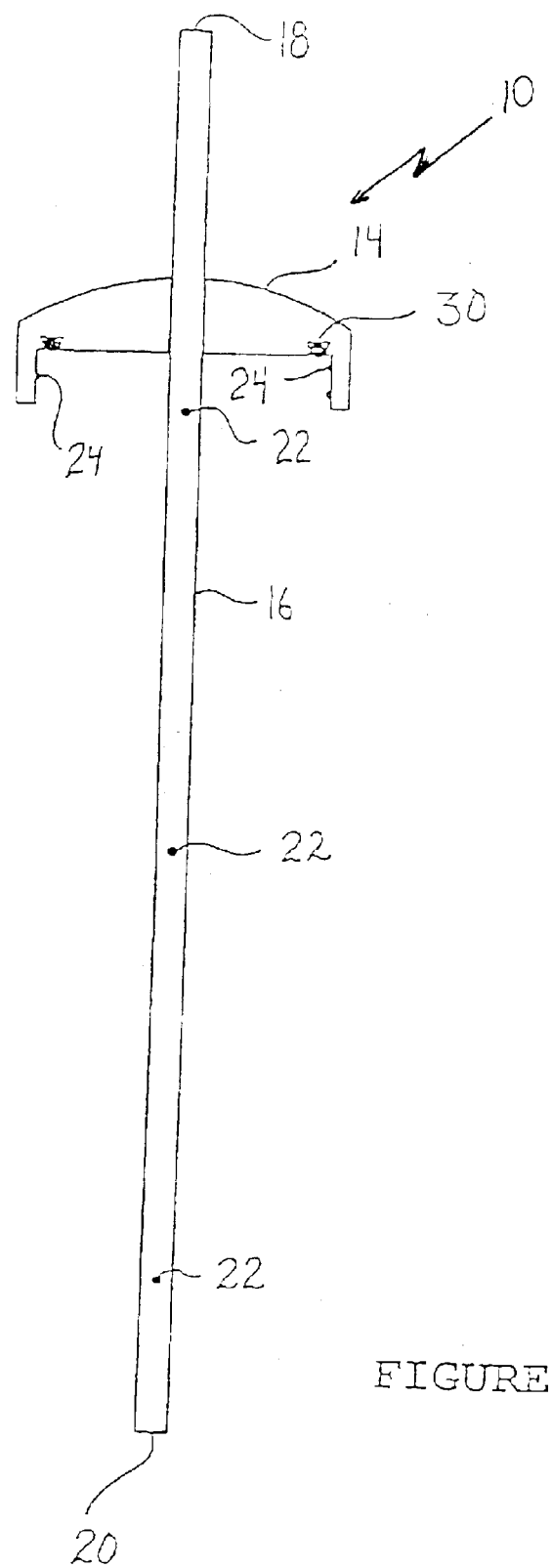
FIG. 1 is a side elevation view, in section, of an apparatus for extracting a representative sample of water, oil and sediment from a container constructed in accordance with the teachings of the present invention.

The preferred embodiment, an apparatus for extracting a representative sample of water, oil and sediment from a container generally identified by reference numeral 10, will now be described with reference to FIGS. 1 through 4.

Structure and Relationship of Parts

Figure 2:
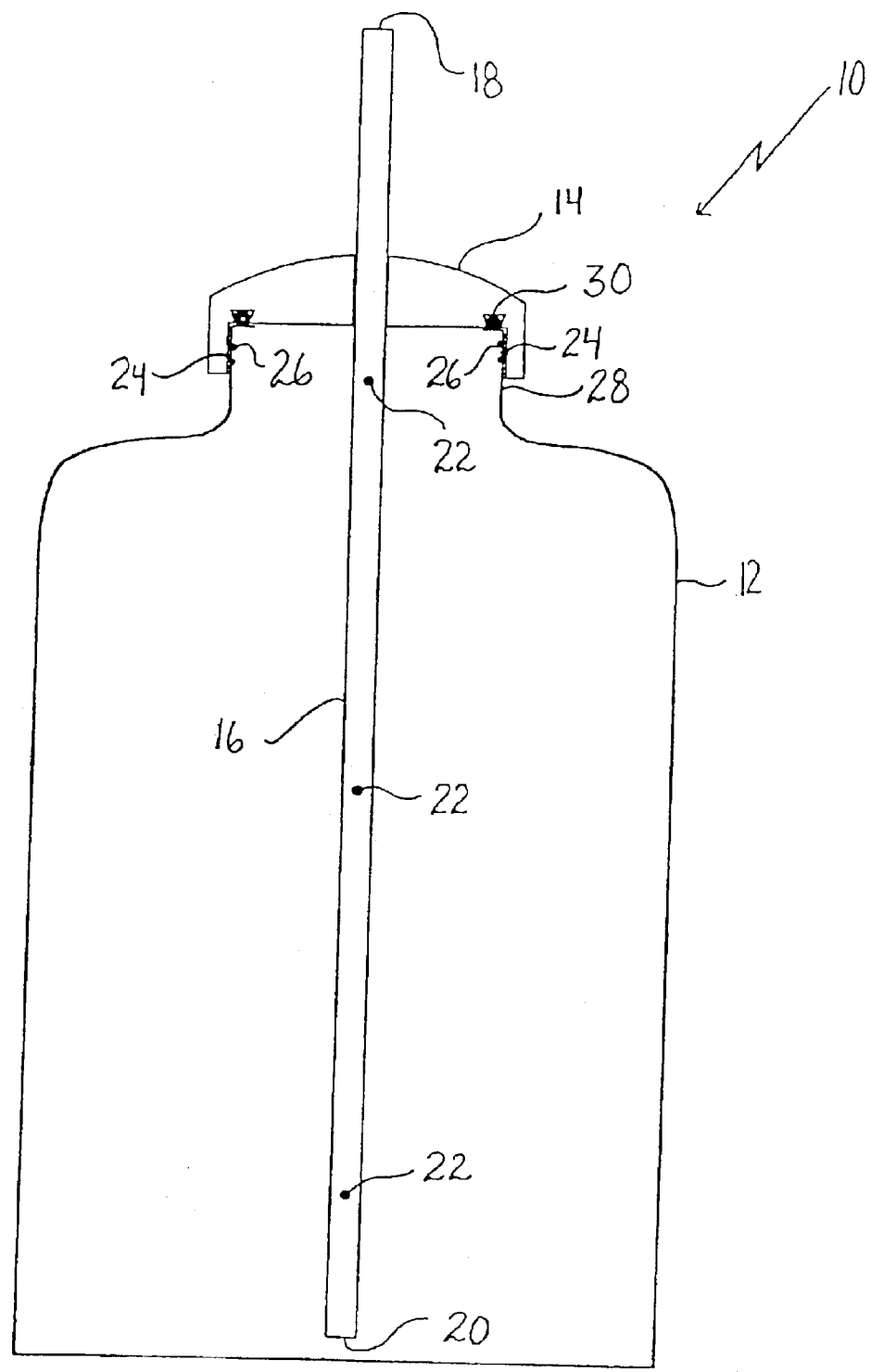
FIG. 2 is a side elevation view, in section, of the apparatus illustrated in FIG. 1, positioned on a container.

Referring to FIG. 1, apparatus 10 is in the form of a container closure 14. Referring to FIG. 2, container closure 14 is adapted to fit onto a resiliently deformable container 12. Container closure 14 has a tube 16 extending therethrough, such that fluids can be extracted from container 12 through tube 16 when closed by closure 14. Referring to FIG. 1, tube 16 has a first end 18 and a second end 20. First end 18 is open to the flow of fluids and second end 20 is closed. Radial inlet ports 22 are positioned at spaced intervals along tube 16 between closure 14 and second end 20 of tube 16. This enables fluids from container 12 to enter tube 16 at several levels through different inlet ports 22 to provide a more representative sample. It is preferred that inlet ports 22 have a combined flow capacity which is less than a flow capacity of tube 16, as it has been found that this helps to further enhance the obtaining of a representative sample.

Referring to FIGS. 1 and 2, in the illustrated embodiment, closure 14 has threads 24 that are adapted to engage with threads 26 on neck 28 of container 12 such that closure 14 can be secured to container 12. It will be appreciated that closure could simply be a rubber stopper and there are other effective ways in which to secure closure 14 to container 12. Closure 14 also has a seal 30 which ensure that fluids can not escape when with closure 14 is threadably engaged to container 12.

Operation

Figure 3:
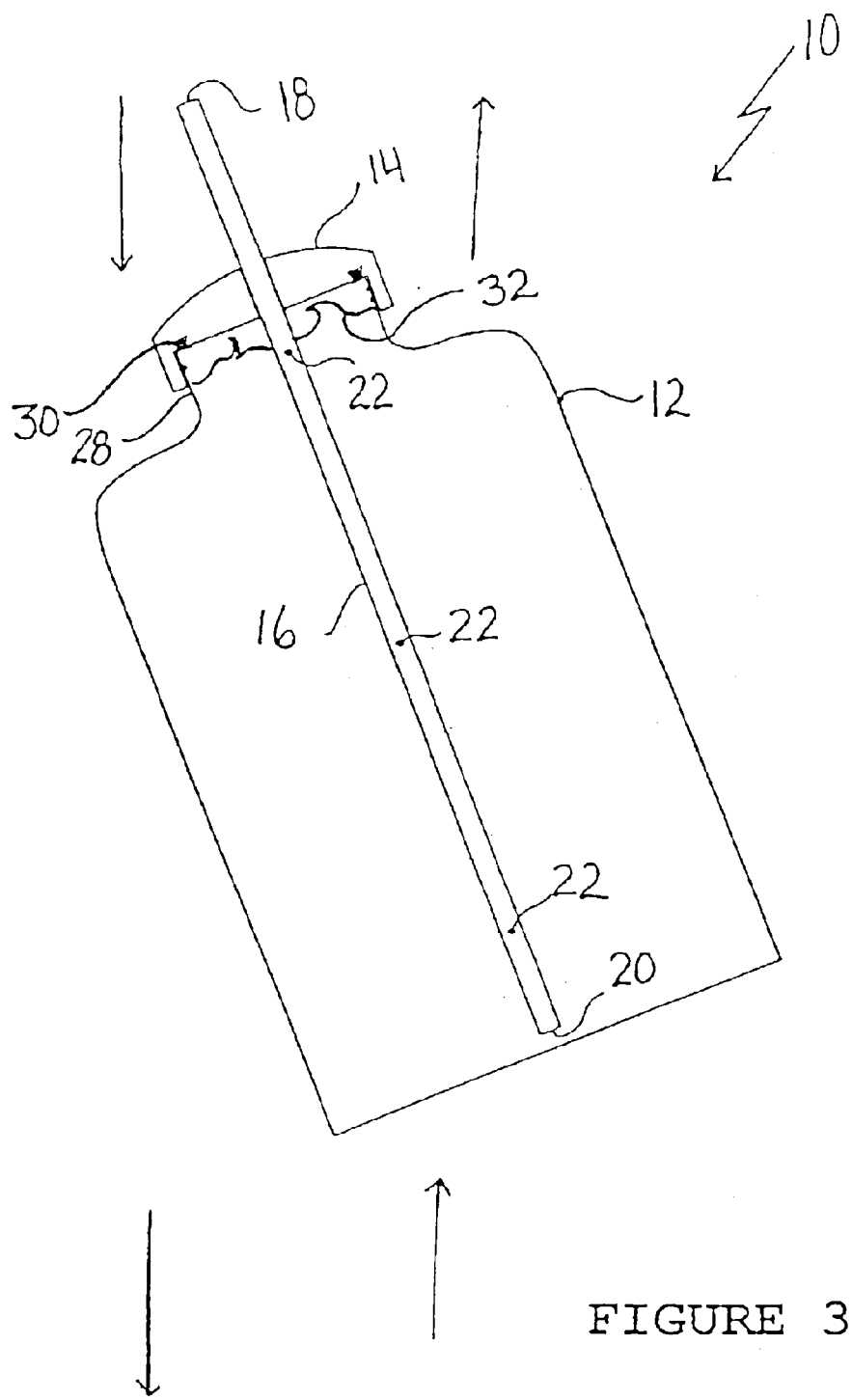
FIG. 3 is a side elevation view of the apparatus illustrated in FIG. 1, being used for an agitation step in accordance with the teachings of the preferred method.
Figure 4:
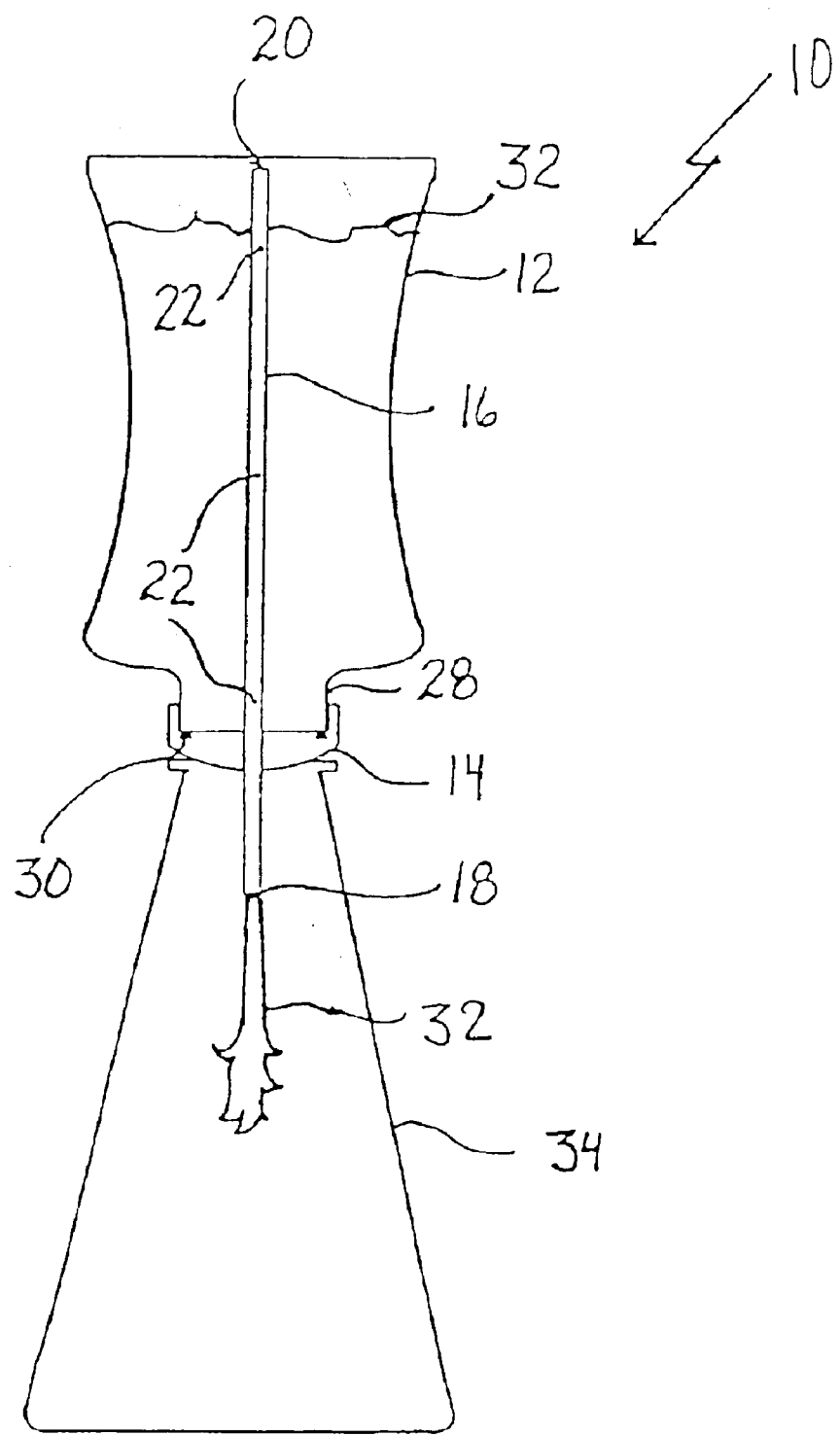
FIG. 4 is a side elevation view of the apparatus illustrated in FIG. 1, with pressure being created by squeezing to force fluids from the container through the tube in accordance with the teachings of the preferred method.

The use and operation of apparatus 10 will now be described with reference to FIGS. 1 through 4. A portion of the fluids 32 produced by an oil well are collected in container 12. Fluids 32 contain a mixture of water, oil and sediment in unknown proportions. Referring to FIG. 3, closure 14 is threadably secured to container 12 so that fluids 32 cannot escape. Container 12 is then agitated to mix fluids 32. Referring to FIG. 4, after agitating fluids 32, container 12 is inverted over a sample tube 34. Container 12 is then squeezed to create sufficient pressure within container 12 to cause a stream of mixed fluids 32 from container 12 to flow out of first end 18 of tube 16. By having fluids 32 enter through inlet ports 22 at spaced intervals along tube 16, a more representative sample is provided. It has been determined through test data that having the fluids exiting container 12 under pressure is much more accurate than pouring. It has also been determined that accuracy is further enhanced when inlet ports 22 have a combined flow capacity which is less than the flow capacity of tube 16.

Test Data

In tests of the apparatus, oil and water mixtures with predetermined sediment and water percentages were used as test samples.

An oil/water mixture containing a known percentage of 88.9% sediment and water was provided. The mixture was agitated in the apparatus for 15 seconds and then squeezed to dispense the mixture into the centrifuge tube. This resulted in a content reading of 89% sediment and water. When the traditional method of mixing the mixture in a sample container and then pouring the mixture into a centrifuge tube was used, the results yielded a reading of only 70% water and sediment content on a first test and of 60% water and sediment content on a second test.

An oil/water mixture containing a known percentage of 50% sediment and water was provided. The mixture was agitated in the apparatus for 15 seconds and then squeezed to dispense the mixture into the centrifuge tube. This resulted in a reading of 49.5% water and sediment content. When the traditional pouring method was used, the result was a reading of only 24% water and sediment content on a first test, and only 15% water and sediment content on a second test.

Cautionary Warning

As mentioned above, the accuracy of the method and apparatus can be improved by adjusting the size of the inlet ports. In most cases this will involve reducing the size of the inlet ports. If the inlet ports are too large relative to the flow capacity of the tube, the inlet ports will contribute fluids in unequal amounts depending upon the positioning of the inlet ports along the length of the tube.

Variations

All initial testing of apparatus 10 was performed with a container 12 that was substantially full. After a series of successful tests with full containers, field tests were expanded. In the course of the further field tests, a number of samples were received in which the sample containers were only partially filled; in some cases less than half filled. It was discovered that when working with the partially filled containers the accuracy dropped substantially. An investigation was conducted to determine the reason for this discrepancy. It was determined that when the container were only partially filled there were too many inlet ports. Apparatus 10 was, therefore, modified so it would work not only with substantially filled containers, but also with partially filled containers.

Figure 5:
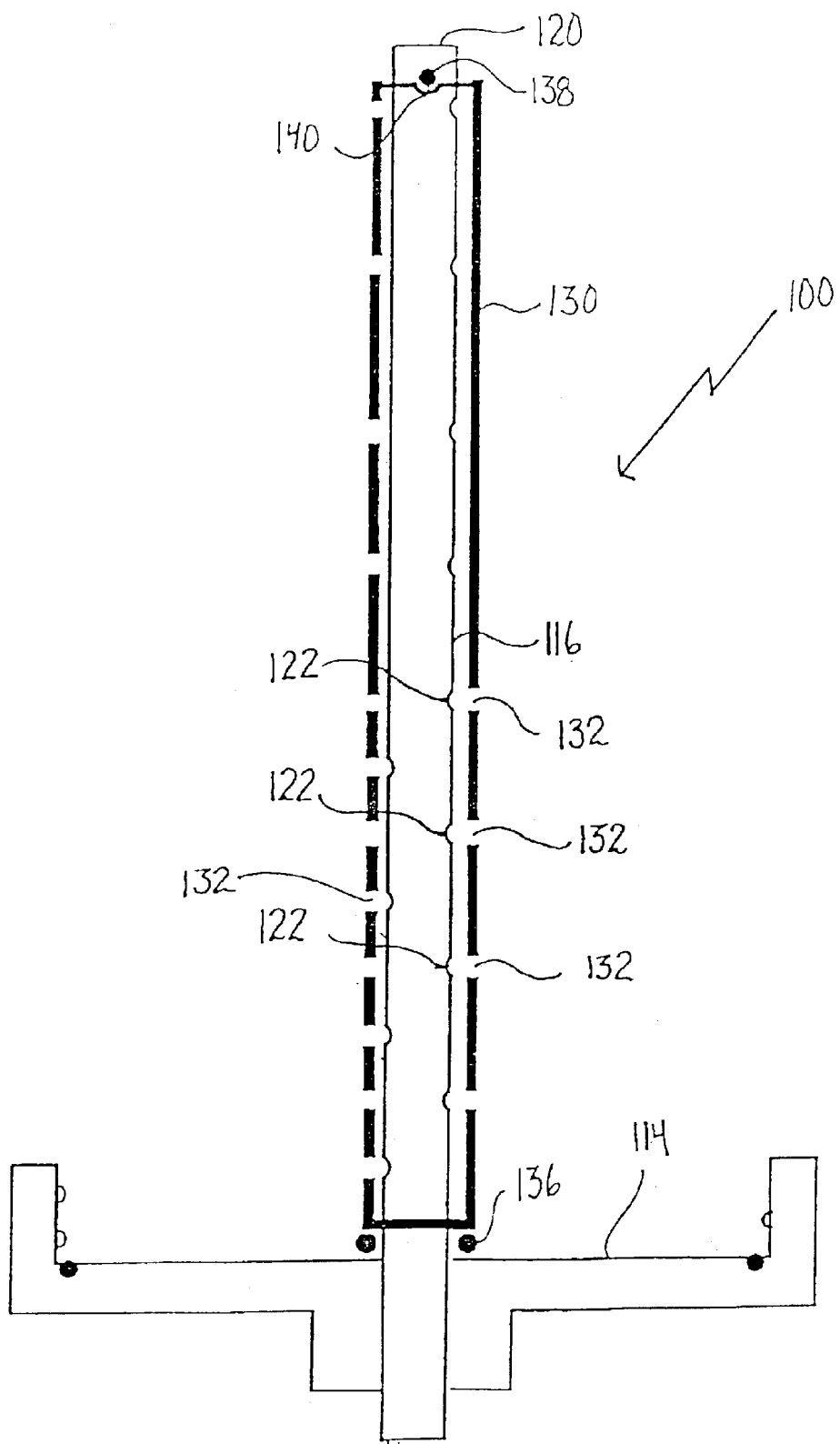
FIG. 5 is a side elevation view, in section, of an alternative embodiment of an apparatus for extracting a representative sample of water, oil and sediment from a container constructed in accordance with the teachings of the present invention, in an inverted orientation.

Referring to FIG. 5, there is illustrated a modified form of apparatus, generally identified by reference numeral 100. Apparatus 100 is in the form, of a container closure 114. Container closure 114 has a tube 116 extending therethrough, such that fluids can be extracted through tube 116 when closure 114 is positioned on a container. Tube 116 has a first end 118 and a second end 120. First end 118 is open to the flow of fluids and second end 120 is closed. Radial inlet ports 122 are positioned at spaced intervals along tube 116 between closure 114 and second end 120 of tube 116.

Figure 6:
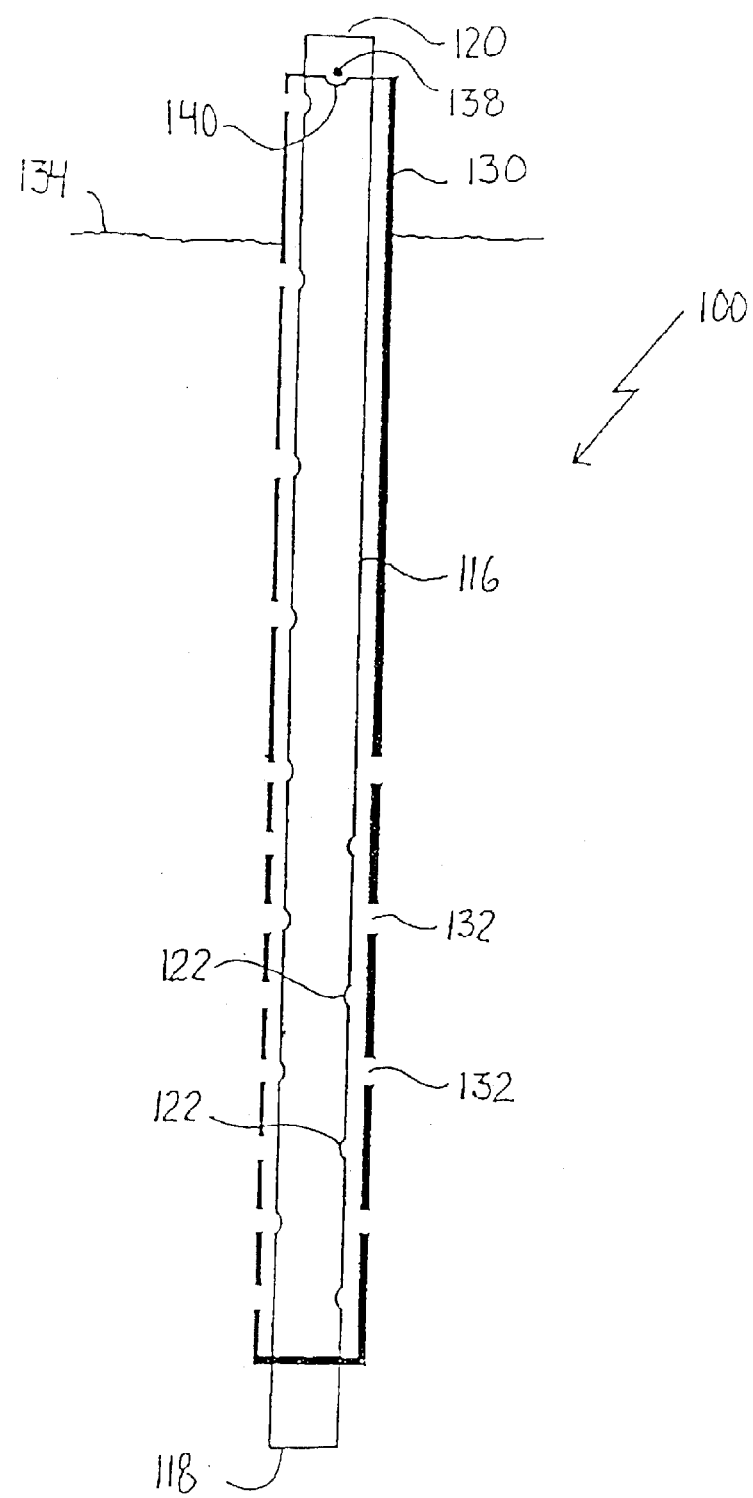
FIG. 6 is a side elevation view, in section, of the apparatus illustrated in FIG. 5, in an inverted orientation with a full flow depth position.
Figure 7:
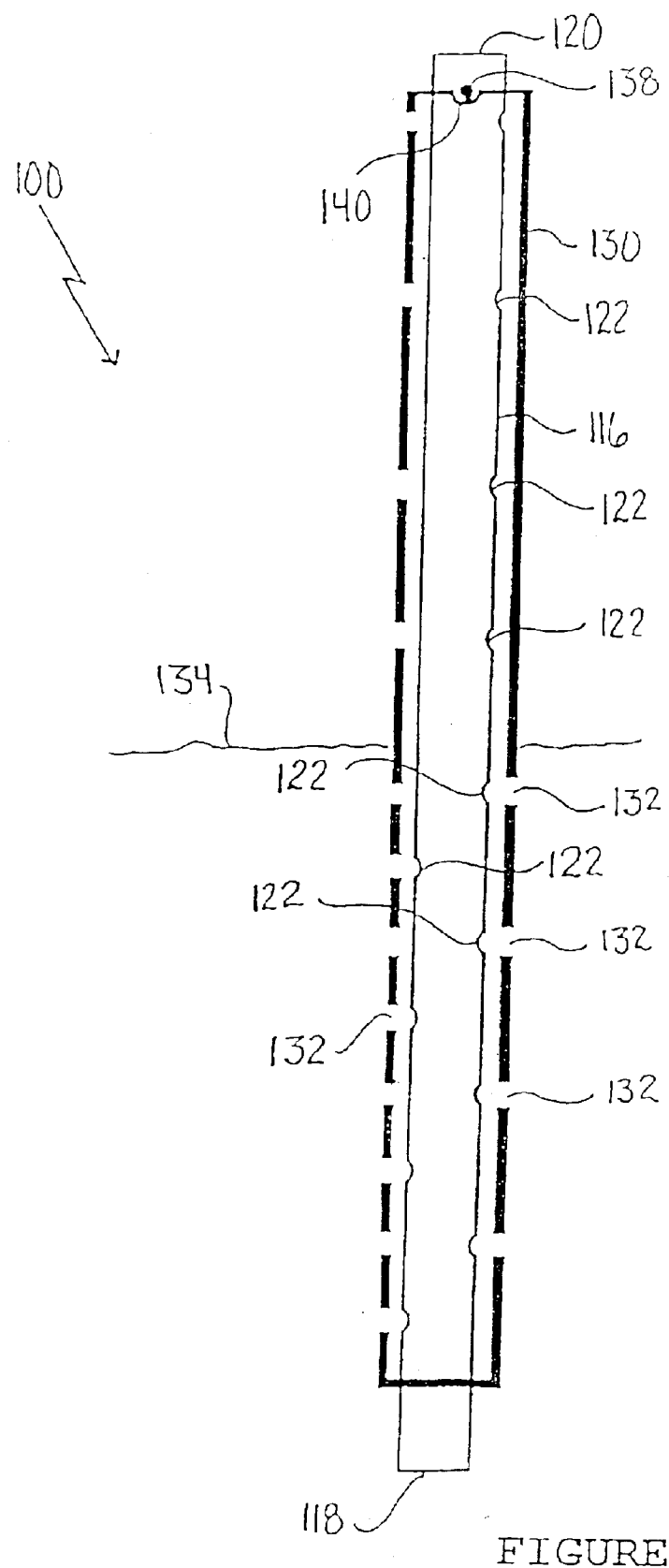
FIG. 7 is a side elevation view, in section, of the apparatus illustrated in FIG. 5, in an inverted orientation with a restricted flow depth position.

A sleeve 130 overlies tube 116. Flow openings 132 are positioned at spaced intervals along sleeve 130. By altering the relative rotational positioning of tube 116 and sleeve 130 the setting of apparatus 100 can be altered from a full flow depth position illustrated in FIG. 6 to a restricted flow depth position illustrated in FIG. 7. A fluid level is indicated by line 134 in both FIGS. 6 and 7. Referring to FIG. 6, when fluid level 134 reflects a substantially full container the full flow depth position is used. In the full flow depth position, flow openings 132 of sleeve 130 are aligned with radial inlet ports 122 of tube 116. This allows flow to enter radial inlet ports 122 along the entire length of tube 116. Referring to FIG. 7, when fluid level 134 reflects a partially filled container the restricted flow depth positioned is used. In the restricted flow depth position, flow openings 132 of sleeve 130 are out of register with radial inlet ports 122 toward second end 120 of tube 116 while still remaining aligned with radial inlet ports 122 toward first end 118 of tube 116. This allows flow to enter radial inlet ports 122 only along a restricted length of tube 116 toward first end 118.

There are three ways of altering the relative positioning of tube 116 and sleeve 130 which are contemplated. Tube 116 can be rotatable with sleeve 130 fixed to closure 114, as illustrated in FIGS. 6 and 7. Tube 116 can be fixed to closure 114 with sleeve 130 rotatably as illustrated in FIG. 5. Tube 116 and sleeve 130 can both be rotatable. Where a space must be left to permit rotation of sleeve 130, it is contemplated that an additional annular seal 136 will be required, as illustrated in FIG. 5, in order to prevent fluids from bypassing flow openings 132.

Although not absolutely essential, it is preferred that instead of relying solely upon friction to maintain the selected relative positioning of sleeve 130 and tube 116, that some form of locking engagement be provided. The locking engagement illustrated is a positioning pin 138 that extends transversely through tube 116 and engages a selected one of several notches 140 in sleeve 130. This form of engagement is particularly suited for the embodiment illustrated in FIG. 5, as annular seal 136 resiliently flexes to provide relative longitudinal movement to make it easier to engage and disengage positioning pin 138 from notches 140. This resilient force also serves to bias positioning pin 138 into engagement with notches 140.

Cautionary Note

The premise behind the present invention is that the instant agitation of the sample ceases, the fluid begins to separate into layers. The intent of the present invention is to use tube 16 or 116 to extract a representative sample by proportional extraction through radial inlet ports 22 or 122 from a column of fluid in container 12. If the fluid is in the process of rapidly separating into oil, water, and sediment layers; proportional extraction through the radial inlet ports results in fluids being extracted proportionately from the column of fluid to still give a representative sample. When determining the size and spacing of the radial inlet ports, a person skilled in the art must study the geometry of the container. With containers having long narrow necks or wide bases, the size and spacing of the radial inlet ports may have to be carefully determined to ensure that there is not a disportionate flow that distorts the sample by drawings disportionately from the oil layer or water layer. The greater the accuracy that the application demands, the more precise the size and positioning of the radial inlet ports must be.

In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be one and only one of the elements.

It will be apparent to one skilled in the art that modifications may be made to the illustrated embodiment without departing from the spirit and scope of the invention as hereinafter defined in the claims.

The embodiments of the invention in which an exclusive property or privilege is claimed are defined as follows:

1. An apparatus for extracting a representative sample of water, oil and sediment from a container, comprising:

a container closure having a tube extending therethrough, such that fluids can be extracted from any closed container through the tube when closed by the closure;

the tube having a first end and a second end, the first end being open to the flow of fluids and the second end being closed; and several radial inlet ports of uniform size being positioned at spaced intervals along the tube between the closure and the second end of the tube, such that fluids from the container enter the tube at several levels through different ones of the inlet ports to provide a more representative sample;

a sleeve overlying the tube;

several flow openings of uniform size being positioned at spaced intervals along the sleeve; and at least one of the tube and the sleeve being rotatable about its longitudinal axis for altering the relative rotational positioning of the tube and the sleeve between a full flow depth position and a restricted flow depth position, such that in the full flow depth position the flow openings of the sleeve are aligned with the radial inlet ports of the tube to allow flow to enter radial inlet ports along the length of the tube, and in the restricted flow depth position the flow openings of the sleeve are out of register with the radial inlet ports toward the second end of the tube while still remaining aligned with the radial inlet ports toward the first end of the tube to allow flow to enter radial inlet ports only along a restricted length toward the first end.

2. The apparatus as defined in claim 1, wherein mechanism is provided for maintaining the relative position of the sleeve and the tube in the full flow depth position and the restricted flow depth position.

* * * * *

UNITED STATES PATENT AND TRADEMARK OFFICE
CERTIFICATE OF CORRECTION

PATENT NO. : 6,820,507 B2
DATED : November 23, 2004
INVENTOR(S) : N.E. Seatter

It is certified that error appears in the above-identified patent and that said Letters Patent is hereby corrected as shown below:

<u>Title page,</u>
Item [76], Inventors, "Alberto" should read -- Alberta --

<u>Column 6,</u>
Line 33-24, "mecha-
　　　　　nism" should read -- means --

Signed and Sealed this

Twenty-sixth Day of April, 2005

JON W. DUDAS
*Director of the United States Patent and Trademark Office*